United States Patent [19]

Gargani

[11] 4,337,206
[45] Jun. 29, 1982

[54] PROCESS FOR PREPARING HIGH PURITY URSODEOXYCHOLIC ACID

[75] Inventor: Pietro Gargani, Milan, Italy

[73] Assignee: Erregierre S.p.A., Bergamo, Italy

[21] Appl. No.: 258,730

[22] Filed: Apr. 29, 1981

[30] Foreign Application Priority Data

May 14, 1980 [IT] Italy .............................. 22033 A/80

[51] Int. Cl.$^3$ .............................................. C07J 9/00
[52] U.S. Cl. ................................................. 260/397.1
[58] Field of Search ..................................... 260/397.1

[56] References Cited

U.S. PATENT DOCUMENTS 4,213,911 7/1980 Attwell et al. ................... 260/397.1
4,282,161 8/1981 Guillenetto et al. ............. 260/397.1

*Primary Examiner*—Elbert L. Roberts
*Attorney, Agent, or Firm*—Stevens, Davis, Miller & Mosher

[57] ABSTRACT

A process for preparing $3\alpha$, $7\beta$-dihydroxy-cholanic acid (I) from $3\alpha$, $7\alpha$-dihydroxy-$\Delta_{11}$-cholenic acid. This starting substance is converted by oxidation and successive reduction into $3\alpha$, $7\beta$-dihydroxy-$\Delta_{11}$-cholenic acid, which is separated in the form of the tris-trimethylsilyl derivative of high purity. The product (I) is obtained by hydrogenating and hydrolyzing the trisilyl derivative.

4 Claims, No Drawings

PROCESS FOR PREPARING HIGH PURITY URSODEOXYCHOLIC ACID

This invention relates to a new industrial process for producing ursodeoxycholic acid (3-alpha-7-beta-dihydroxycholanic acid) of high purity, and in particular not contaminated by the chenodeoxycholic acid epimer (3-alpha-7-alpha-dihydroxycholanic acid).

Ursodeoxycholic acid is known as a product which has assumed increasing interest in the therapeutic field as new types of activity have been found for it. At present, ursodeoxycholic acid is used as a solubiliser for bile calculi, for lowering the percentage of cholesterol in the blood, for lowering glycaemia, as a diuretic, and as an accelerant for the lipid metabolism.

The processes used at the present time for producing ursodeoxycholic acid all essentially fall within the same scheme, which comprises oxidising chenodeoxycholic acid to 3α-hydroxy-7-ketocholanic acid (II), which is hydrogenated to ursodeoxycholic acid or 3α,7β-dihydroxy-cholanic acid (I)

The final stage in which the acid (II) is hydrogenated to ursodeoxycholic acid (I) always leads to a mixture of ursodeoxycholic acid and chenodeoxycholic acid in the proportions of about 80:20, from which the chenodeoxycholic acid is difficult to eliminate.

In this respect, various methods have been proposed for purifying the mixture resulting from the hydrogenation, these methods being more or less efficient and more or less complicated, but all constitute a considerable burden on the process in terms of products, apparatus, time and consequently cost.

A new extremely selective process has now been found, and forms the subject matter of the present invention, which enables ursodeoxycholic acid to be prepared directly at a purity suitable for pharmaceutical uses, without any subsequent purification process being necessary.

The new process again uses as its starting substance 3α,7β-dihydroxy-Δ11-cholenic acid (IV), obtained generally from cholic acid. However, it then follows a path which is completely different from the process of the known art, by way of intermediate products which are all new compounds.

The new process is essentially represented by the following reaction scheme:

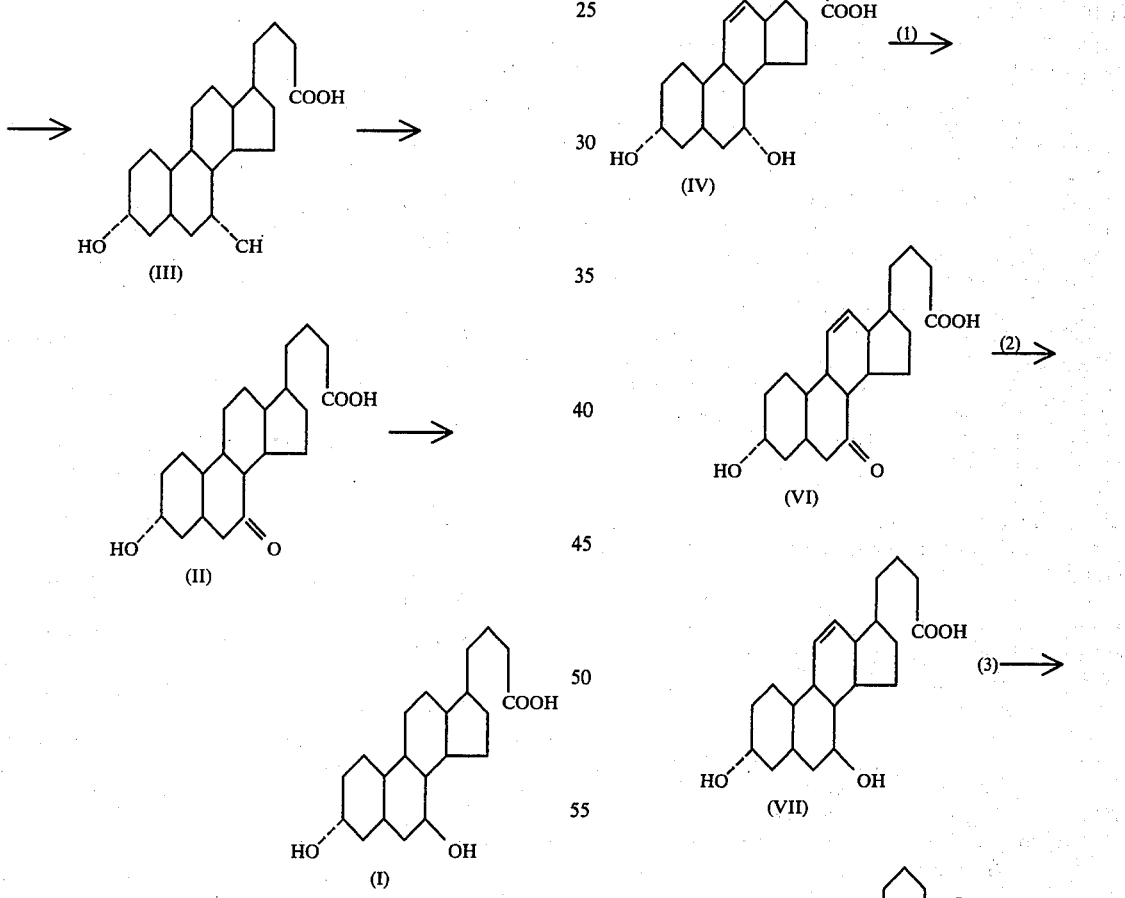

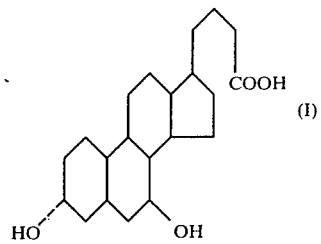

Stage (1) of the process shown schematically heretofore represents oxidation of 3α,7α-dihydroxy-Δ₁₁-cholenic acid (IV) to the corresponding 3α-hydroxy-7-Keto-Δ₁₁-cholenic acid (VI). The oxidation is preferably carried out with an alkaline chromate in an acetic acid solution buffered with an alkaline acetate.

The temperature of the reaction mixture must be kept between 0° and 20° C.

Stage (2) comprises the selective hydrogenation of the 7-keto group without saturation of the double $\Delta_{11}$ bond, to form a mixture constituted mainly (80–90%) by 3α,7β-dihydroxy-Δ₁₁-cholenic acid (VII) and a smaller percentage (10–20%) of 3α,7α-dihydroxy-Δ₁₁-cholenic acid. This selective reduction is preferably carried out with metal sodium or metal potassium in an inert organic solvent at the mixture reflux temperature. Suitable organic solvents are the lower aliphatic alcohols containing 3-4 carbon atoms.

The acid mixture separated at the end of stage (2) is redissolved in a suitable organic solvent, and subjected to stage (3) for preparing the tris-trimethylsilyl derivative, by treatment with a suitable silanising agent. The organic solvents preferred in this stage are for example dimethylformamide, dimethylsulphoxide, acetonitrile, benzene, toluene, acetone, methylethylketone, methylisobutylketone and the like. The silanising agent used can be bis-trimethylsilurea, hexamethyldisilazane, bis-trimethyl-silylacetamide and the like, at a temperature of between 60° and 100° C.

Under these conditions the tris-trimethylsilyl derivative of 3α,7β-dihydroxy-Δ₁₁-cholenic acid is formed, which precipitates, whereas the tris-trimethylsilyl derivative of 3α,7α-dihydroxy-Δ₁₁-cholenic acid remains in solution.

From the tris-trimethylsilyl derivative of the pure 3α,7β-dihydroxy-Δ₁₁-cholenic acid, 3α,7β-dihydroxycholanic acid is obtained in an equally pure state, and in particular free from the 3α,7α-dihydroxy-cholanic acid epimer.

This latter passage can be carried out in two alternative ways which are equivalent in terms of cost and yield. The first of these is hydrogenating compound (VIII) to the corresponding tris-trimethylsilyl derivative of cholanic acid, and then hydrolysing the trimethylsilyl groups. Alternatively, compound (VIII) can be hydrolysed to give pure 3α,7β-dihydroxy-cholenic acid, which is then hydrogenated to the corresponding 3α,7β-dihydroxy-cholanic acid. This alternative is preferred in practice.

In either case, effective hydrogenation conditions are obtained by operating in an alcoholic solution with a supported Pd catalyst at a temperature of between 50° and 100° C. and a pressure of 2-5 atm. gauge.

Hydrolysis of the trimethylsilyl derivative is carried out in an aqueous acid solution at a temperature of between 50° and 100° C., whether done before or after hydrogenation. The product (I) is separated from the final reaction mixture by crystallisation.

Some embodiments are given hereinafter in order to clarify the description and to make the process according to the invention more easily reproducible, but these are in no case intended as limiting.

EXAMPLE 1

32 g of $K_2CrO_4$ dissolved in 60 ml of $H_2O$ are added over a time of 1 hour without exceeding 10° C., to 50 g of 3α,7α-dihydroxy-Δ₁₁-cholenic acid dissolved in 500 ml of acetic acid containing 100 g of sodium acetate.

After the addition, the mixture is left stirring for 10 hours. After this time, it is diluted with $H_2O$ until sharply turbid. It is stirred for 1 hour, then filtered, well squeezed and dried. The product has the following characteristics:

M.P. 202°–203° C., $[\alpha]_D^{20}$ 23±2 (C 1 dioxane).

Elementary analysis for $C_{24}H_{36}O_4$: Calculated: C 74.10%; H 9.26%. Found: C 74.15%; H 9.23%.

50 grams of 3a-hydroxy-7-keto-Δ₁₁-cholenic acid dissolved in 750 ml of isopropanol are treated under boiling conditions with 50 g of metal sodium.

After the addition, the mixture is left under reflux for 2 hours, and the isopropanol is then distilled off, replacing it gradually by $H_2O$.

After completely eliminating the isopropanol, the solution is cooled and acidified with dilute HCl to precipitate 3α,7β-dihydroxy-Δ₁₁-cholenic acid, which is crystallised from ethyl acetate. The product, which contains about 15% of 3α,7α-dihydroxy-Δ₁₁-cholenic acid, is then placed in 200 ml of dimethylformamide and treated with 50 g of bis-trimethylsilurea. The mixture is heated to 90° for 1 hour, then cooled to 0° C. In this manner, the pure tris-trimethylsilyl derivative of 3α,7β-dihydroxy-Δ₁₁-cholenic acid precipitates, and is collected by filtration and washed with dimethylformamide. When a sample of the product, which is unstable in that it is easily hydrolysed by moisture, is rapidly dried it shows a M.P. of 130°–132° C.

A sample hydrolysed with HCl in the presence of ethyl acetate and water and then crystallised from ethyl acetate has the following characteristics:

M.P. 208–210, $[\alpha]_D^{20}$+58±1 (C 1 EtOH).

Alkalimetric strength 99%.

Elementary analysis for $C_{24}H_{38}O_4$: Calculated: C 73.80%; H 9.80%. Found: C 73.65%; H 9.15%.

The tris-trimethylsilyl derivative of 3α,7β-dihydroxy-Δ₁₁-cholenic acid is well squeezed and then dissolved in 400 ml of methanol, and hydrogenated at 4 atm. gauge and at 60° in the presence of 5% Pd/C for a period of 8 hours. At the end of this it is cooled, the Pd/C is filtered off, and the methanol solution is concentrated to a small volume. The residue is taken up in 500 ml of ethyl acetate and 100 ml of $H_2O$, and acidified with HCl.

This mixture is heated to 50° to cause complete desilanisation, and the aqueous phase is then separated. The organic phase is washed to neutral with $H_2O$, and then concentrated until precipitation begins.

It is cooled to 0° and the pure 3α,7β-dihydroxy-5β-cholanic acid is filtered and washed with ethyl acetate, then dried under vacuum. 28 g of product are obtained having the following characteristics:

M.P. 201°–203° C., $[\alpha]_D^{20}$ 60±1 (C 1 EtOH).

Alkalimetric strength 99%–100%.

Elementary analysis for $C_{24}H_{40}O_4$: Calculated: C 73.40%; H 10.25%. Found: C 73.35%; H 10.30%.

3α,7α-dihydroxy-5β-cholanic acid 0.2%.

EXAMPLE 2

100 grams of 3α-hydroxy-7-keto-$\Delta_{11}$-cholenic acid obtained as described in the previous example are dissolved in 200 ml of secondary butanol, and reduced by treating with 100 g of metal sodium under boiling conditions.

After the addition, the mixture is left under reflux for 2 hours, all the secondary butanol is distilled off, and the residue is dissolved in H$_2$O.

The solution is acidified to precipitate the 3α,7β-dihydroxy-$\Delta_{11}$-cholenic acid. The process then continues as in example No. 1.

EXAMPLE 3

75 grams of 3α-hydroxy-7-keto-$\Delta_{11}$-cholenic acid dissolved in 200 ml of n.butanol are treated with 80 g of metal potassium under boiling conditions. After the addition, the mixture is left under reflux for 1 hour, then the n-butanol is distilled off under vacuum and replaced by water.

3α,7β-dihydroxy-$\Delta_{11}$-cholenic acid precipitates from the aqueous alkaline solution by acidification, and is filtered off, crystallised from ethyl acetate and dried.

The product is then suspended to acetonitrile and treated with 60 g hexamethyldisilazane. The mixture is heated under reflux for 2 hours, and is then cooled to 0° overnight. In this manner, the pure tris-trimethylsilyl derivative of 3α,7β-dihydroxy-$\Delta_{11}$-cholenic acid precipitates, and is filtered of and washed well with acetonitrile.

The wet product is dissolved in 500 ml of ethyl acetate and 100 ml of water, the solution is then acidified with HCl and heated to 50° for 30 minutes.

It is allowed to stand, and the aqueous phase is then separated and discarded, whereas the organic phase is washed to neutral, concentrated to a small volume and cooled to 0° C. Pure 3α,7β-dihydroxy-$\Delta_{11}$-cholenic acid crystallises, is filtered, washed with ethyl acetate and dried.

50 grams of pure 3α,7β-dihydroxy-$\Delta_{11}$-cholenic acid are dissolved in 400 ml of ethanol and hydrogenated in the presence of Pd/C at 60° for 10 hours. After filtering off the Pd/C, the solution is concentrated to one third of its volume and diluted with deionised water. 3α,7β-dihydroxy-5β-cholanic acid precipitates, and is filtered off and dried. 48 g of product are obtained having the characteristics described in example 1.

EXAMPLE 4

250 grams of 3α,7β-dihydroxy-$\Delta_{11}$-cholenic acid impure by virtue of the presence of 3α,7α-dihydroxy-$\Delta_{11}$-cholenic acid (about 15%) and obtained as described in example 1 are dissolved in 1000 ml of toluene, and 250 g of bis-trimethylsilylurea are added thereto. The mixture is heated to 100° for 1 hour and then cooled to 0° C. The pure tris-trimethylsilyl derivative of 3α,7β-dihydroxy-$\Delta_{11}$-cholenic acid is collected by filtration, and is hydrogenated directly as described in example 1.

EXAMPLE 5

120 grams of 3α,7β-dihydroxy-$\Delta_{11}$-cholenic acid impure by virtue of the presence of 3α,7α-dihydroxy-$\Delta_{11}$-cholenic acid and obtained as described in example 1 are dissolved in 600 ml of methylisobutylketone, and 120 g of bis-trimethylsilylacetamide are added thereto.

The mixture is heated to 80° for one hour, then cooled overnight to 0°. The pure tris-trimethylsilyl derivative of 3α,7β-dihydroxy-$\Delta_{11}$-cholenic acid is filtered off, and is washed firstly with methylisobutylketone and then with toluene. The wet product is hydrogenated and treated in the same manner as described in example 3.

I claim:

1. A process for preparing high purity 3α,7β-dihydroxy-cholanic acid from 3α,7α-dihydroxy-$\Delta_{11}$-cholenic acid, comprising
   (1) oxidizing the 3α,7α-dihydroxy-$\Delta_{11}$-cholenic acid to 3α-hydroxy-7-keto-$\Delta_{11}$-cholenic acid with an alkaline chromate in a buffered acetic acid solution,
   (2) selectively reducing the obtained 7-keto compound with metallic sodium or metallic potassium in an inert organic solvent, at the reflux temperature of the reaction mixture, to 3α,7β-dihydroxy-$\Delta_{11}$-cholenic acid,
   (3) reacting this product with a silanising agent in an organic solvent at a temperature between 60° and 100° C. to form the corresponding tris-trimethylsilyl derivative,
   (4) hydrolyzing the tris-trimethylsilyl derivative in an aqueous acid solution at a temperature of between 50° C. and 100° C. to obtain the free acid, and
   (5) hydrogenating the free acid in an alcoholic solution with a supported Pd catalyst at a temperature of between 50° C. and 100° C. and a pressure of 2–5 atm.

2. A process for preparing high purity 3α,7β-dihydroxy-cholanic acid from 3α,7α-dihydroxy-$\Delta_{11}$-cholenic acid, comprising
   (1) oxidizing the 3α,7α-dihydroxy-$\Delta_{11}$-cholenic acid to a 3α-hydroxy-7-keto-$\Delta_{11}$-cholenic acid with an alkaline chromate in a buffered acetic acid solution,
   (2) selectively reducing the obtained 7-keto compound with metallic sodium or metallic potassium in an inert organic solvent, at the reflux temperature of the reaction mixture, to 3α, 7β-dihydroxy-$\Delta_{11}$-cholenic acid,
   (3) reacting this product with a silanising agent in an organic solvent at a temperature between 60° and 100° C. to form the corresponding tris-trimethylsislyl derivative,
   (4) hydrogenating the tris-trimethyl derivative in an alcoholic solution with a supported Pd catalyst at a temperature of between 50° C. and 100° C. and a pressure of 2–5 atm. to the corresponding tris-trimethylsilyl derivative of the 3α,7β-dihydroxy-cholanic acid, and
   (5) hydrolyzing this product in an aqueous acid solution at a temperature of between 50° C. and 100° C.

3. Process according to claim 1 wherein the silanising agent is selected from the group consisting of bis-trimethylsilurea, hexamethyldisilazane, and bis-trimethylsilylacetamide.

4. Process according to claim 2 wherein the silanising agent is selected from the group consisting of bis-trimethylsilurea, hexamethyldisilazane, and bis-trimethylsilylacetamide.